Figure 1:
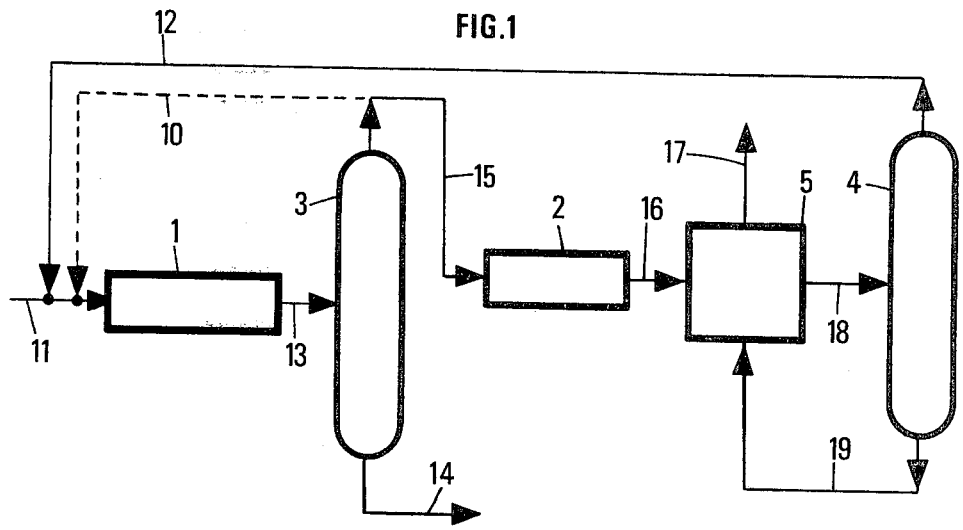

United States Patent [19]

Torck et al.

[11] 4,324,924

[45] Apr. 13, 1982

[54] PROCESS FOR REMOVING ISOBUTENE FROM A $C_4$ CUT AND PRODUCING METHYL TERT-BUTYL ETHER

[75] Inventors: Bernard Torck, Boulogne sur Seine; Alaio Convers; Didier Duee, both of Rueil Malmaison; Paul Mikitenko, Noisy Le Roi, all of France

[73] Assignee: Institut Francais du Petrole, Rueil-Malmaison, France

[21] Appl. No.: 143,242

[22] Filed: Apr. 24, 1980

[30] Foreign Application Priority Data

Apr. 24, 1979 [FR] France ................ 79 10399

[51] Int. Cl.$^3$ .................. C07C 41/06; C07C 7/00
[52] U.S. Cl. .................. 568/697; 585/800; 568/699
[58] Field of Search ............... 568/697, 699; 585/800

[56] References Cited

U.S. PATENT DOCUMENTS

| | | | |
|---|---|---|---|
| 3,726,942 | 4/1973 | Louder | 568/697 X |
| 3,979,461 | 9/1976 | Anciallotte et al. | 568/697 |
| 4,144,138 | 3/1979 | Rao et al. | 568/697 X |
| 4,198,530 | 4/1980 | Wentzheimer et al. | 568/697 |
| 4,219,678 | 8/1980 | Obenaus et al. | 568/697 |

*Primary Examiner*—Howard T. Mars
*Attorney, Agent, or Firm*—Millen & White

[57] ABSTRACT

Process for producing methyl tert-butyl ether (MTBE) by reacting methanol with the isobutene present in a $C_4$ cut in a proportion from 10 to 60%, wherein said cut, admixed with methanol is contacted, in a first reaction zone, with an acid catalyst in the conditions of etherification of isobutene by methanol unit 93 to 98% of the isobutene has been converted, the reaction product is fractionated under at least 10 bars to a bottom fraction consisting essentially of MTBE and a top fraction which is contacted, in a second reaction zone, with an acid catalyst, under the conditions of etherification of isobutene by methanol, until at least 99% of the initial isobutene has been converted, the resulting product is washed with water and separated into a residual $C_4$ cut which is discharged and an aqueous phase wherefrom methanol is recovered by distillation.

11 Claims, 2 Drawing Figures

PROCESS FOR REMOVING ISOBUTENE FROM A C₄ CUT AND PRODUCING METHYL TERT-BUTYL ETHER

BACKGROUND OF THE INVENTION

This invention relates to the production of methyl tertbutyl ether (M T B E) by reacting methanol with the isobutene contained in a $C_4$ cut.

Such a reaction is known as being balanced and accordingly, it is difficult to obtain high conversion rates. It is however possible to obtain them by making use of relatively complex techniques which considerably increase the cost of the operation. In most cases, only a relatively low isobutene proportion of the $C_4$ cut is converted.

However, this is not acceptable for certain utilizations of the n-butenes of the residual $C_4$ cut, such for example as the synthesis of maleic anhydride or the production of 1-butene polymers or copolymers.

The invention has for object to obtain a high conversion rate of the isobutene, resulting in the obtainment of a $C_4$ cut free to a large extent from isobutene, which can be used particularly for the specific above-mentioned applications.

Figure 2:
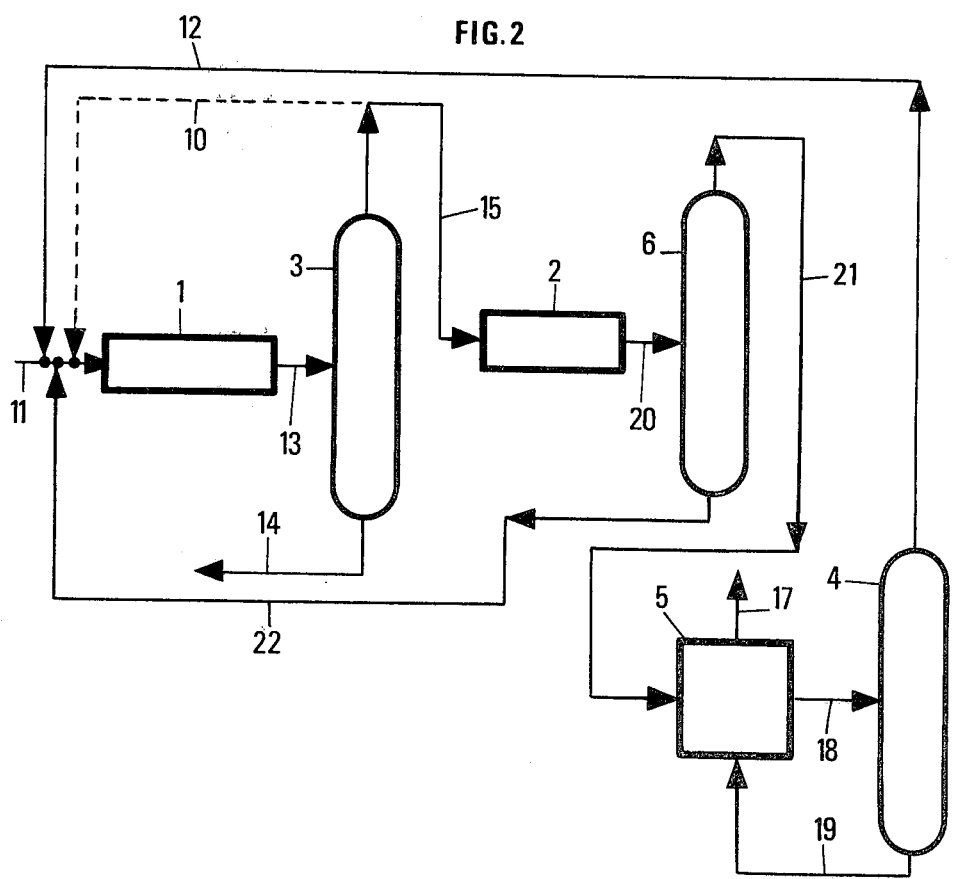

The invention will be better understood by comparison with prior art processes, and with reference to FIGS. 1 and 2. When making use of a single reactor (1) or of an assembly including several reactors, it has been possible to obtain, by mere passage over the catalyst, isobutene conversions of from 93 to 98% with molar ratios methanol/isobutene at the reactor inlet (1) sufficiently low (for example from 1.02 to 2, preferably from 1.05 to 1.3) for avoiding the requirement, for recovering methanol, of a distillation column in addition to column 3 operated under high pressure, for example 10 to 30 bars; substantially all the methanol passes at the top and it is accordingly useless to make use of an additional distillation column for fractionating the bottom effluent from column 3 to a methanol-MTBE azeotrope, at the top, and a purified MTBE stream, at the bottom. In order to increase the isobutene conversion, the process described in French Patent Specification No. 79 03937 of Feb. 14, 1979 recycles the distillate from column 3 to the inlet of reactor (1) through line 10, shown in dashed line in the drawings. It is thus possible to obtain conversion rates of about 98–99%. If still higher conversion rates are desired without additional reactors, the molar ratio methanol/isobutene must be much higher. Particularly by mere passage of the charge over the catalyst, it is required that the molar ratio $CH_3OH$/isobutene be about from 9 to 10 in order to obtain a conversion rate of 99.8%. This results in serious disadvantages due to the fact that the effluent from the reactor then contains substantial amounts of methanol which have to be separated from the MTBE and from the $C_4$ cut. Such a separation is difficult and expensive, irrespective of the operating mode.

DETAILED DISCUSSION

According to the invention, it is possible to obtain such high conversion rates by making use of another process scheme whose essential element is an additional reactor (2) which contains a catalyst of the same nature and wherethrough is passed the distillate, from the fractionation column (3), of the $C_4$ cut and the MTBE. The effluent from this reactor may be treated in two different ways: it may be directly supplied to the water-washing section (5) to recover the methanol excess which is recycled to the reactor after distillation (FIG. 1) or to a second fractionation column (6) operated under relatively low pressure (1 to 9 bars, preferably 3 to 6 bars) such that the major part of methanol is recovered from the bottom of the column and recycled to the reactor with the MTBE.

The process of the invention comprises the following essential steps:

(a) a mixture of methanol with a hydrocarbon $C_4$ cut containing from 10 to 60% by weight of isobutene is passed through at least a first reaction zone, in contact with an acid catalyst, under the conditions of etherification of isobutene by methanol and the reaction is continued up to the conversion of 93 to 98% of the isobutene, the molar ratio methanol/isobutene at the inlet being selected higher than the stoichiometrical ratio of 1:1 and such that this ratio may reach a value higher than 1:1 at the outlet, preferably from 3:1 to 20:1, (b) the product obtained from step (a) is fractionated under a pressure of at least 10 bars; there is recovered from the top a mixture consisting essentially of residual $C_4$ cut and methanol in proportions substantially identical to those of the product from step (a) and, from the bottom, a product consisting essentially of methyl tert-butyl ether, which is discharged, (c) the top product from step (b) is supplied to a second reaction zone, in contact with an acid catalyst, under the conditions of etherification of isobutene by methanol, and the reaction is continued until achievement of an overall conversion of the isobutene of at least 99% (with respect to the isobutene introduced in step (a), and (d) the product from step (c) is washed with water and there is recovered separately an aqueous phase and a residual $C_4$ hydrocarbon phase, which is discharged, while the aqueous phase is distilled to obtain separately recovered methanol and water.

According to an improved embodiment of this technique, the product from step (c) is fractionated under a pressure from 1 to 9 bars, to produce:

(i) a top stream consisting essentially of a residual $C_4$ cut carrying therewith a minor proportion of methanol, which is supplied to step (d), and (ii) a bottom stream containing methanol, methyl tert-butyl ether and a minor proportion of residual $C_4$ cut, which is fed to the reaction zone of step (a).

When operating according to this improved embodiment, there is easily obtained a bottom stream wherein the molar ratio methanol/MTBE is higher than 1; if this condition is not achieved, the recycling to the reactor of the first step would have no effect or a noxious one. It is preferable that this ratio be higher than 3 and for example from 3 to 20.

There is already known a process comprising two successive reaction zones with an intermediate separation of the MTBE formed in the first reaction zone (French Patent No. 2,272,063). In this process, it is not contemplated to wash with water the effluent from the second reactor for recovering methanol therefrom; it is not mentioned either to proceed to an intermediate separation under a pressure of at least 10 atmospheres. Finally, in the case of the second embodiment of the invention, it is not suggested to recycle to the first reactor the product from the bottom of the second distillation column: such a recycling would in fact not produce a good result due to the composition of the product of the second reactor, containing more MTBE than methanol (in moles).

According to FIG. 1, illustrating an example, there is introduced in reactor 1, through line 11, methanol and C$_4$ cut containing saturated hydrocarbons (butane and isobutane) and unsaturated hydrocarbons (isobutene and n-butenes), the isobutene content being, for example, from 10 to 60% by weight, and preferably from 18 to 48% by weight. The molar ratio methanol/isobutene at the inlet of reactor 1, after admixture with the recycled streams from line 12 and optionally line 10 is from 1.02:1 to 2:1, preferably from 1.05:1 to 1.3:1. This ratio is of importance; it is selected in accordance with the desired isobutene conversion rate in reactor 1, which ranges from 93 to 98%, so that, at the outlet of reactor 1, the molar ratio methanol/isobutene is higher than 1:1, preferably from 3:1 to 20:1.

The temperature is from 50° to 100° C. and the pressure from 10 to 30 bars. The catalyst is an acid catalyst of known type, for example a sulfonic ion exchange resin in acid form. The reaction is allowed to continue until the isobutene is converted in a proportion from 93 to 98%, as above-mentioned.

The effluent from reactor 1 is fed through line 13 to the distillation column 3 operated under a pressure from 10 to 30 bars, preferably from 14 to 20 bars. In these conditions, the top effluent contains the residual C$_4$ cut and a relatively high proportion of methanol, whereas the bottom effluent, discharged from line 14, may consist of MTBE freed from methanol to a large extent. The composition of the methanol/C$_4$ hydrocarbons azeotropes is well known; it has the higher methanol content as the pressure is higher, it is thus easy to determine in each case the minimum pressure to be used in column 3, so that methanol is found substantially completely in the top fraction.

The top effluent is fed, through line 15, to reactor 2. The molar ratio methanol/isobutene is then higher than 1, preferably from 3:1 to 20:1. The pressure and the temperature are selected in the range mentioned for the first reactor. It is thus possible to obtain a very high conversion rate for isobutene, higher than 99% and, in most cases, higher than 99.5% for the assembly of the two reactors.

The effluent is fed to the water-washing unit 5, through line 16. The water amount is, for example, from 0.1 to 10 times, by volume, the amount of the effluent from reactor 2. The washing product separates in two phases: the residual C$_4$ cut substantially free from methanol, discharged through line 17 and the aqueous phase which is fed through line 18 to the distillation column 4. The water recovered at the bottom may be fed back, through line 19, to the washing unit 5, whereas the methanol may be recycled, through line 12, to reactor 1. Small amounts of MTBE may be present with this recycled methanol.

The diagram of FIG. 2 is similar, from a general point of view, to that of FIG. 1, except that a distillation column 6 is inserted between reactor 2 and the washing unit 5. In this case, the effluent from reactor 2 is fed, through line 20, to column 6 which is operated under as low a pressure as possible, from 1 to 8 bars. For practical reasons, it is preferred to proceed under a pressure from 3 to 6 bars. This column provides, at the top, a mixture of residual C$_4$ cut and methanol whose MTBE content is much smaller than it was in line 16 of FIG. 1. This mixture is fed to the washing unit 5 through line 21. The bottom current, which contains MTBE, undistilled methanol and, optionally, a portion of the residual C$_4$ cut, may be fed back to the inlet of reactor 1, through line 22.

The catalyst is for example one of those described in the U.S. Pat. Nos. 2,480,940 and No. 3,037,052.

EXAMPLE 1

This example is illustrated by FIG. 1 (line 10 is not in operation).

Through a reactor (1) containing 10 m$^3$ of catalyst consisting of ion exchange resin of the Amberlyst 15 type, there is passed 14 t/h of a C$_4$ cut containing 49% by weight of isobutene, the remainder consisting essentially of butane, isobutane and n-butenes, 3.9 t/h of fresh methanol and 0.5 t/h of methanol which is the distillate from the water-methanol fractionation column (4). This corresponds to a molar ratio of methanol to isobutene of 1.14. The temperature is 65° C. and the pressure 15 bars. The conversion rate of isobutene is 96% at the outlet of the reactor. The reactor effluent (molar ratio methanol/isobutene=about 4.8) is fractionated in a distillation column 3 operated under a pressure of 16 bars abs. From the bottom there is withdrawn 10.4 t/h of MTBE of a purity degree of 96.3%. From the top of said column, there is withdrawn 8 t/h of a distillate containing 8.5% by weight of methanol. This distillate (molar ratio methanol/isobutene=about 4.3) is introduced in an additional reactor (2) containing 2.5 m$^3$ of the same resin. The temperature is 55° C. and the pressure 15 bars.

The overall conversion of isobutene is thus equal to 99.8%. The effluent from this reactor containing 6.6% by weight of methanol is fed to a water-washing section to recover methanol. The residual C$_4$ cut contains 0.2% by weight of isobutene and 3.8% by weight of MTBE. Methanol, which distilles from the top of column (4), contains 18% by weight of MTBE (distillation under atmospheric pressure).

EXAMPLE 2

This example is illustrated by FIG. 2. The temperature and pressures are the same as in example 1.

A reactor (1) containing 12 m$^3$ of Amberlyst 15 resin, is fed with 14 t/h of the same C$_4$ cut as in example 1, containing 49% by weight of isobutene, 3.9 t/h of fresh methanol, 0.13 t/h of methanol which is the distillate from the water-methanol fractionation column, and 1.2 t/h of the bottom product from column (6) containing 48.2% by weight of methanol, 33.1% by weight of MTBE and the remainder of C$_4$ cut. This leads to a molar methanol/isobutene ratio at the inlet of reactor (1) identical to that of the preceding case. The conversion rate of the isobutene is also identical i.e. 99.6%. The reactor effluent having the same methanol/isobutene ratio as in example 1, is fractionated in a distillation column (3), operated under 16 bars abs. From the bottom, there is withdrawn 10.7 t/h of MTBE having the same purity degree as in the preceding case. From the top, there is withdrawn 8.4 t/h of a distillate containing 8% by weight of methanol (with the same methanol/isobutene ratio as in example 1). This distillate is introduced in an additional reactor (2) containing 3.0 m$^3$ of the same resin. The overall conversion of isobutene is now equal to 99.8%. The effluent from this reactor is fed to a fractionation column operated under a pressure of 4 bars. The product withdrawn from the bottom is fed to the reactor as abovementioned. From the top there is withdrawn 7.2 t/h of a distillate, containing 1.8% by weight of methanol, which is fed to the water-washing section. Taking account of this methanol content which is about one third of that of the preceding case, the investments and the operating costs of the washing section are decreased. The residual C₄ cut issued from the washing section contains, as in the preceding case, 0.2% of isobutene but the MTBE content is substantially zero. By operating in this manner, the MTBE production has been substantially increased.

What is claimed is:

1. A process for producing methyl tert-butyl ether and recovering a substantially isobutene- and methanol-free C₄ cut by reacting methanol with a hydrocarbon C₄ cut comprising from 10 to 60% by weight of isobutene, said process comprising the steps of:
   (a) contacting a mixture of methanol, said C₄ cut, and a recycle stream as hereinafter defined, in a first reaction zone, with an acid catalyst, under conditions for etherification of isobutene with methanol, and converting from 93 to 98% of isobutene, the methanol/isobutene molar ratio being maintained higher than 1:1 at the inlet and at the outlet of said first reaction zone;
   (b) fractionating the effluent from step (a) under a pressure of at least 10 bars, and separately recovering an overhead fraction having a methanol/isobutene molar ratio higher than 1:1 and a bottoms product fraction comprising methyl tert-butyl ether, and discharging said bottoms product fraction;
   (c) contacting the overhead fraction from step (b) with an acid catalyst, in a second reaction zone, under conditions for etherification of isobutene with methanol such that an overall isobutene conversion of at least 99% is effected;
   (d) fractionating the effluent from step (c) under a pressure of 1–9 bars, and separately recovering an overhead fraction consisting essentially of C₄ hydrocarbons and a minor proportion of methanol, and a bottoms fraction containing methanol, methyl tert-butyl ether and a minor proportion of C₄ hydrocarbons, and having a methanol/methyl tert-butyl ether molar ratio higher than 1:1, said bottoms fraction being recycled as said recycle stream to step (a); and
   (e) washing at least a portion of the overhead fraction from step (d) with water, and separately recovering a substantially isobutene- and methanol-free C₄ cut, and a methanol-containing aqueous wash stream.

2. A process according to claim 1, wherein the molar ratio methanol/isobutene at the inlet of the reaction zone of step (a) is selected so as to obtain a value from 3:1 to 20:1 of the corresponding ratio at the outlet of said reaction zone.

3. A process according to claim 2, wherein said ratio, at the inlet, is selected from 1.05:1 to 1.3:1.

4. A process according to claim 1, wherein a portion of the overhead fraction from step (b) is fed back to the reaction zone of step (a).

5. A process according to claim 1, wherein the pressure in step (b) is from 14 to 20 bars.

6. A process according to claim 5, wherein in step (d), the pressure is from 3 to 6 bars.

7. A process according to claim 1, wherein in step (d) the pressure is from 3 to 6 bars.

8. A process according to claim 1, wherein said water fraction is recycled to step (e).

9. A process according to claim 1, wherein in step (d), said methanol/methyl tert-butyl ether molar ratio is from 3:1 to 20:1.

10. A process according to claim 1, which further comprises fractionating the methanol-containing wash stream from step (e), and separately recovering a methanol fraction and a water fraction, said methanol fraction being recycled to step (a).

11. A process according to claim 1, wherein the methanol/isobutene molar ratio of steps (a) and (b) is from 1.02:1 to 2:1.

* * * * *